United States Patent [19]

Motomura et al.

[11] Patent Number: 5,173,608

[45] Date of Patent: Dec. 22, 1992

[54] METHOD FOR CORRECTING POSITIONAL SHIFT OF GAMMA CAMERA APPARATUS AND POSITIONAL SHIFT CORRECTING APPARATUS THEREOF

[75] Inventors: Nobutoku Motomura; Takashi Ichihara, both of Ootawara, Japan

[73] Assignee: Kabushiki Kaisha Toshiba, Kawasaki, Japan

[21] Appl. No.: 659,551

[22] Filed: Feb. 22, 1991

[30] Foreign Application Priority Data

Feb. 23, 1990 [JP] Japan ..................................... 2-43597
Sep. 12, 1990 [JP] Japan .................................. 2-240145

[51] Int. Cl.$^5$ ............................................. G01T 1/164
[52] U.S. Cl. .......................... 250/363.09; 250/363.07; 250/369; 250/363.04
[58] Field of Search .................... 250/363.04, 363.02, 250/363.07, 363.09, 369; 364/413.24

[56] References Cited

U.S. PATENT DOCUMENTS 4,281,382  7/1981  Knoll et al. .................... 250/363.07
4,582,995  4/1986  Lim et al. ....................... 250/363.07

Primary Examiner—Carolyn E. Fields
Attorney, Agent, or Firm—Oblon, Spivak, McClelland, Maier & Neustadt

[57] ABSTRACT

In a gamma camera apparatus, positional shifts contained in an output coordinate matrix of a gamma-ray detector by a method comprising the steps of: positioning a reference RI (radio isotope) source at a first reference position the gamma-ray detector so as to obtain a first positional-information coordinate output from the gamma-ray detector; processing the first positional-information coordinate output indicative of a second reference position with respect to the matrix output derived from the detector so as to produce positional correction data; acquiring a third positional-information coordinate output from the detector while injecting a radio isotope into a biological body under medical examination; and, correcting the third positional-information coordinate output based upon the positional correction data.

18 Claims, 11 Drawing Sheets

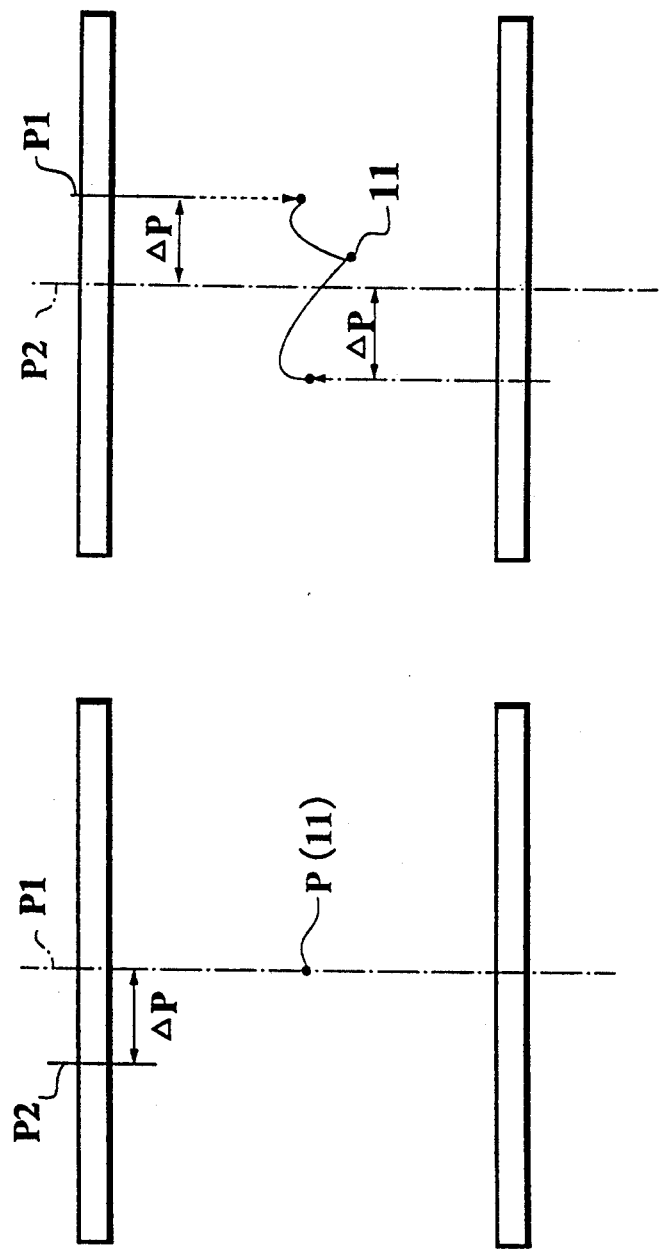

CEL-DATA CORRECTION

CEL-DATA CORRECTION $X = f(x, y)$
$Y = g(x, y)$

METHOD FOR CORRECTING POSITIONAL SHIFT OF GAMMA CAMERA APPARATUS AND POSITIONAL SHIFT CORRECTING APPARATUS THEREOF

BACKGROUND OF THE INVENTION

1. Field of the Invention

The present invention relates to an apparatus and a method for correcting a positional shift containing in a positional-information coordinate output in a matrix form derived from a gamma camera apparatus, e.g., a single photon emission computerized tomographic (SPECT) apparatus.

2. Description of the Related Art

An overall construction of a typical gamma camera apparatus is represented in FIGS. 1 and 2. This gamma camera apparatus is constructed of a couch unit 1 which includes a couch 3 for supporting a biological body 2 under medical examination, e.g., a patient. The couch 3 is movable both a vertical direction Z (height) and a horizontal direction X by way of, for example, a height adjusting mechanism 4. A head portion of the biological body 2 is fixed by a headrest 5, and the biological body 2 into which a predetermined medicine containing a radio isotope (RI) has been injected lies on the couch 3. The gamma camera apparatus further includes a gantry unit 6 having a dome 7 for guiding the biological body 2. Around this dome 7, three sets of detectors (namely gamma cameras) 8A to 8C rotatably provided to detect gamma rays emitted from the radio isotope injected into the biological body 2. The gamma-ray detectors 8A to 8C are arranged, as shown in FIG. 3, in such a manner that these detectors 8A to 8C are equidistantly separated by 120° with each other. It should be noted that an effective field for detecting gamma rays is defined by a region surrounded by a diameter "R" and a depth "l" within this dome 7.

While each of detectors 8A, 8B and 8C is rotated by 120° around the biological body 2 with the above-described arrangement, since the gamma rays may be detected by these detectors 8A to 8C over 360° range, a tomographic image of a desired portion within the biological body 2 under medical examination may be obtained based upon the detected gamma-ray data. The gamma camera apparatus having such an arrangement is known as a SPECT (single photon emission computerized tomography) apparatus.

Generally speaking, in the SPECT apparatus with the above-described three sets of gamma-ray detectors, three detectors 8A to 8C are rotated around a "common" rotation center "P". Assuming now that a perpendicular line "L" passes from this common rotation center "P" to an incident surface of each detector 8A to 8C, a point of intersection "P$_l$" between the perpendicular line "L" and the incident surface of the detector is referred to as a geometrical center". In FIG. 3, reference numerals 9A to 9C indicate collimators.

On the other hand, a projection image of a biological body under medical examination medically measured by a gamma camera is obtained as numerical data with respect to each pixel of a matrix, i.e., an output signal matrix of a gamma-ray detector. FIG. 4 represents an output signal matrix of a gamma-ray detector (i.e., gamma camera) by which a relationship between an incident position of a gamma ray onto the detector 8 (8A, 8B or 8C), and a center position "P$_2$" of an output signal matrix of the detector 8 may be understood. Also, another relationship between an output from the detector 8 and a gamma-ray incident position onto the detector 8 has been corrected with having a linearity, as shown in FIG. 5. It should be understood that the above-described center position "P$_2$" on the output signal matrix of the detector 8 must be coincident with the geometrical center position "P$_1$" of the detector 8 with respect to the positional information in order to obtain a correct diagnostic tomographic image of a biological body.

FIGS. 6A and 6B illustrate the reason why the matrix's center position "P$_2$" must be coincident with the geometrical center position "P$_1$". It is assumed that as shown in FIG. 6A, a point-shaped RI (radio isotope) source 11 is positioned at a rotation center "P" of the detector 8, and a positional shift "P" is present between the geometrical center position "P$_1$" and the center position "P$_2$" detected as the output signal of the detector 8. Projection data of the point-shaped RI source 11 appears on a gamma-ray detector. When this projection data is back-projected onto a matrix (i.e., output coordinate signals from the detector 8) so as to obtain a tomographic image from this projection data, the projection data of the point-shaped RI source 11 is back-projected onto another position which is positionally shifted by "ΔP" from the geometrical center position "P$_1$" as shown in FIG. 6B. As a consequence, a ring-shaped artifact may be formed on a reconstructed image, which requires an offset correction with respect to the center position "P$_2$" on the output signal matrix of the detector 8.

As previously described, since the geometrical center position "P$_1$" of the respective gamma-ray detector is not always coincident with the matrix's center position "P$_2$" thereof in the conventional SPECT apparatus, there is problem that a ring-shaped artifact may happen to occur in the resultant tomographic image. To the contrary, it will be most probably conceived that the conventional SPECT apparatus could be assembled by performing proper fine adjustments on these center positions "P$_1$" and "P$_2$". However, there is another difficulty that highly positional alignment is necessarily required so as to achieve the above-described center coincidence.

The present invention has been made in an attempt to solve the above-described problems and has an object to provide an apparatus and a method for performing an offset correction in order to make coincident between a geometrical center position of a gamma-ray detector and a center position of an output signal matrix thereof in a gamma camera apparatus.

SUMMARY OF THE INVENTION

To achieve the above-described objects, according to the present invention, a method for correcting a positional shift containing a positional-information coordinate output in a matrix form derived from a gamma camera apparatus having at least one gamma-ray detector (8A:8B:8C), comprising the steps of:

positioning a reference RI (radio isotope) source (11) at a first reference position (P;P$_l$) with respect to the gamma-ray detector (8A:8B:8C) so as to obtain a first positional-information coordinate output ($x_a, y_a$) from the gamma-ray detector (8A:8B:8C);

processing the first positional-information coordinate output ($x_a, y_a$) based upon a second positional-information coordinate output ($x_0, y_0$) indicative of a second reference position (P2) with respect to the matrix output derived from the detector (8A:8B:8C) so as to produce positional correction data $(x_a-x_0; y_a-y_0)$;

acquiring a third positional-information coordinate output (X;Y) from the detector 98A:8B:8C) while injecting a radio isotope into a biological body (2) under medical examination; and, correcting the third positional-information coordinate output (X,Y) based upon the positional correction data $(x_a-x_0; y_a-y_0)$.

Furthermore, a gamma camera apparatus, according to the present invention, comprises:

at least first gamma-ray detector means (8:30) for first detecting gamma-rays radiated from a reference RI (radio isotope) source (11) positioned at a first reference position (P:P1) with respect to the first gamma-ray detector means (8:30) to obtain a first positional-information coordinate output $(x_a; y_a)$ in a matrix form, and also for secondly detecting gamma rays emitted from a radio isotope injected into a biological body (2) under medical examination to obtain a second positional-information coordinate output (X,Y) in a matrix form; and, positional-data processing means (40) for processing the first positional-information coordinate output $(x_a, y_a)$ based upon a third positional-information coordinate output $(x_0, y_0)$ in a matrix form indicative of a second reference position (P2) with respect to a matrix output derived from the first gamma-ray detector means (8:30) so as to produce positional correction data $(x_a-x_0; y_a-y_0)$, and also for correcting the second positional-information coordinate output (X,Y) based on the positional correction data $(x_a-x_0; y_a-y_0)$, whereby positional shifts contained in the second positional-information correction output (X,Y) are removed.

BRIEF DESCRIPTION OF THE DRAWINGS

The present invention will be more readily understood on reading the following description with reference to the accompanying drawings, in which:

FIGS. 6A and 6B are illustration for explaining the positional shift occurring between the geometrical center position and matrix's center position;

DETAILED DESCRIPTION OF THE PREFERRED EMBODIMENTS

Basic Idea

Before describing various preferred embodiments, a basic idea of the present invention will now be summarized.

In a basic arrangement of a SPECT apparatus according to the present invention, it is now assumed that a point-shaped RI (radio isotope) source is positioned at the geometical center position "P1" of the first gamma-ray detector 8A, an output signal, or a first positional-information coordinate output $(x_a, y_a)$ from this gamma-ray detector 8A is measured. It should be noted that an output signal of a gamma-ray detector 8 is obtained as a pixel value in a matrix form, and also another output signal, or a second positional-information coordinate output $(x_0, y_0)$ with respect to a center of this matrix is obtained from the detector 8.

Subsequently, the second positional-information coordinate output $(x_0, y_0)$ is subtracted from the first positional-information coordinate output $(x_a, y_a)$, whereby positional correction data is obtained as follows:

$$x_a-x_0 \text{ and } y_a-y_0.$$

This positional correction data is utilized as offset (positional shift) correction data. Thereafter, a third positional-information coordinate output (X,Y) is acquired from the first detector 8A while injecting a radio isotope into the biological body 2 under medical examination. Finally, the following offset correction is executed for the third positional-information coordinate output (X,Y) based upon the offset correction data:

$$X-(x_a-x_0) \text{ and } Y-(y_a-y_0).$$

As a consequence, the geometrical center position "P1" can be coincident with the matrix's center position "P2" by performing the above-described offset correction.

The point-shaped RI source may be positioned at the rotation center position "P" with respect to these detectors 8A to 8C, instead of the geometrical center position. "P1".

POSITIONAL-SHIFT CORRECTION METHOD

Figure 7A:
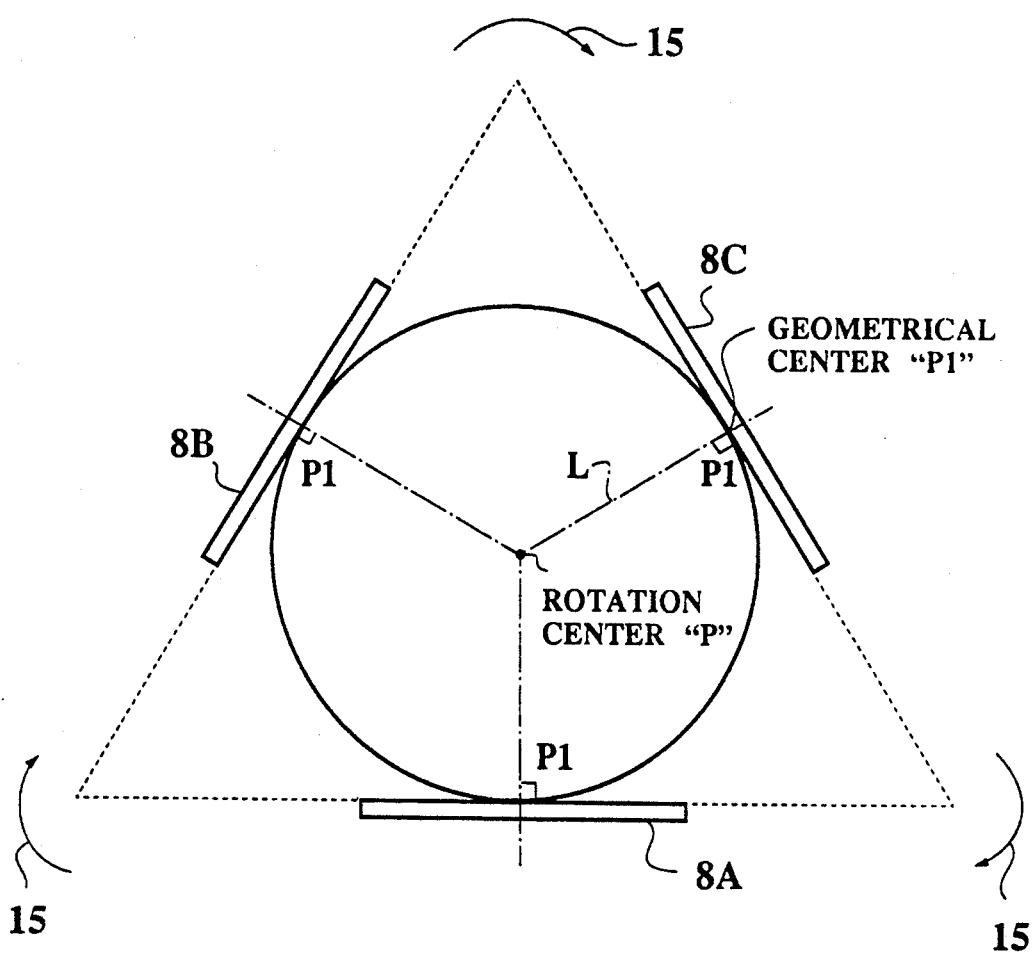
FIGS. 7A and 7B are a front view and a side view of a major portion of a SPECT apparatus capable of performing an offset correction method according to a preferred embodiment of the present invention.
Figure 7B:
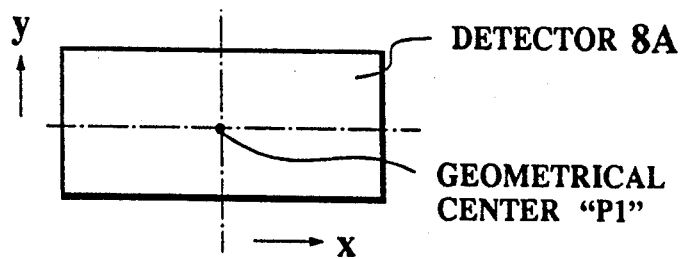
Figure 8:
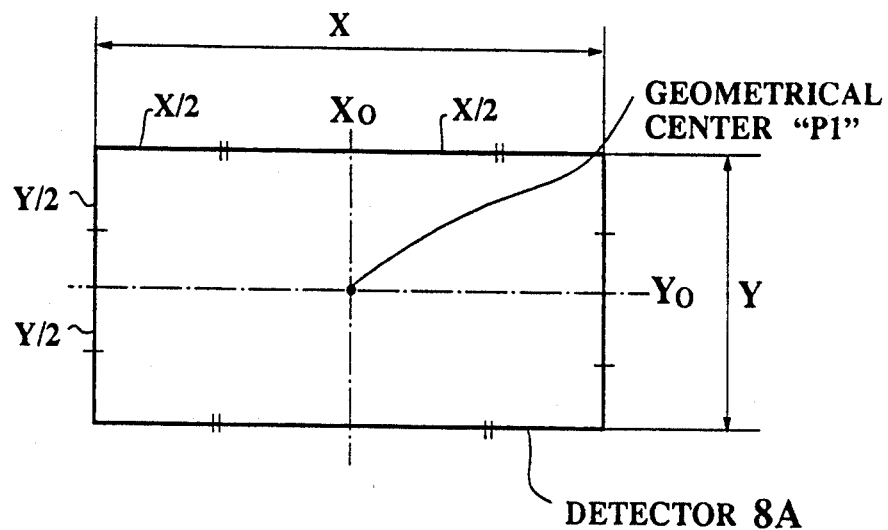
FIG. 8 and 9 are front views of a gamma-ray detector employed in the SPECT apparatus shown in FIG. 7.
Figure 9:
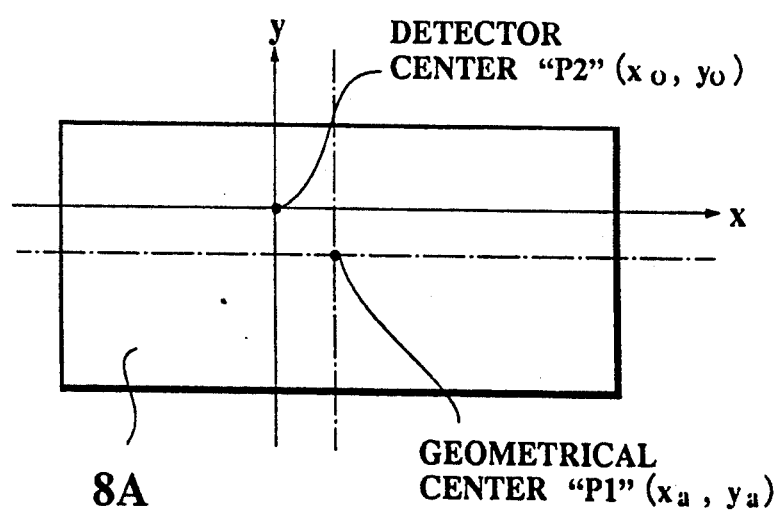

Referring now to FIGS. 7 to 9, a positional-shift correction method, according to a preferred embodiment of the present invention, employing the above-described basic idea will be described in detail.

Figure 1:
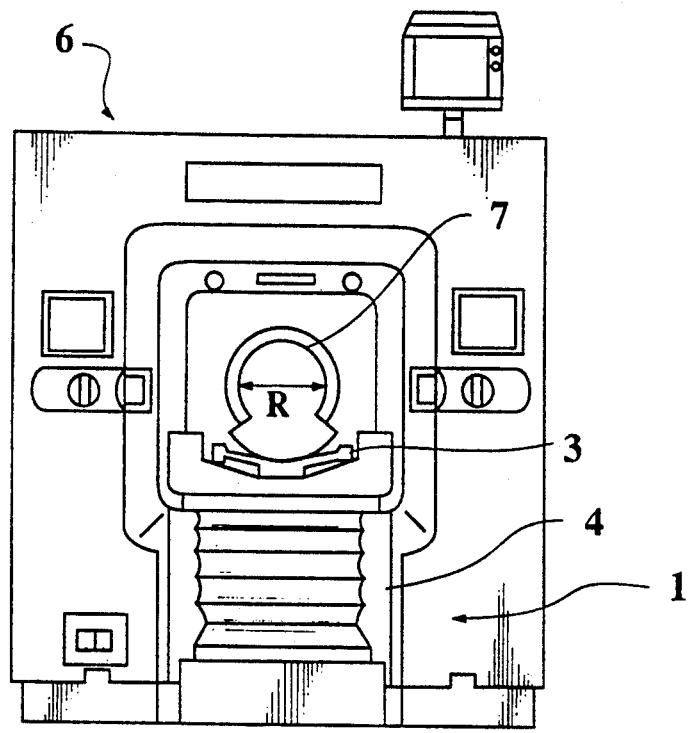
FIG. 1 is a front view of the conventional SPECT apparatus.
Figure 2:
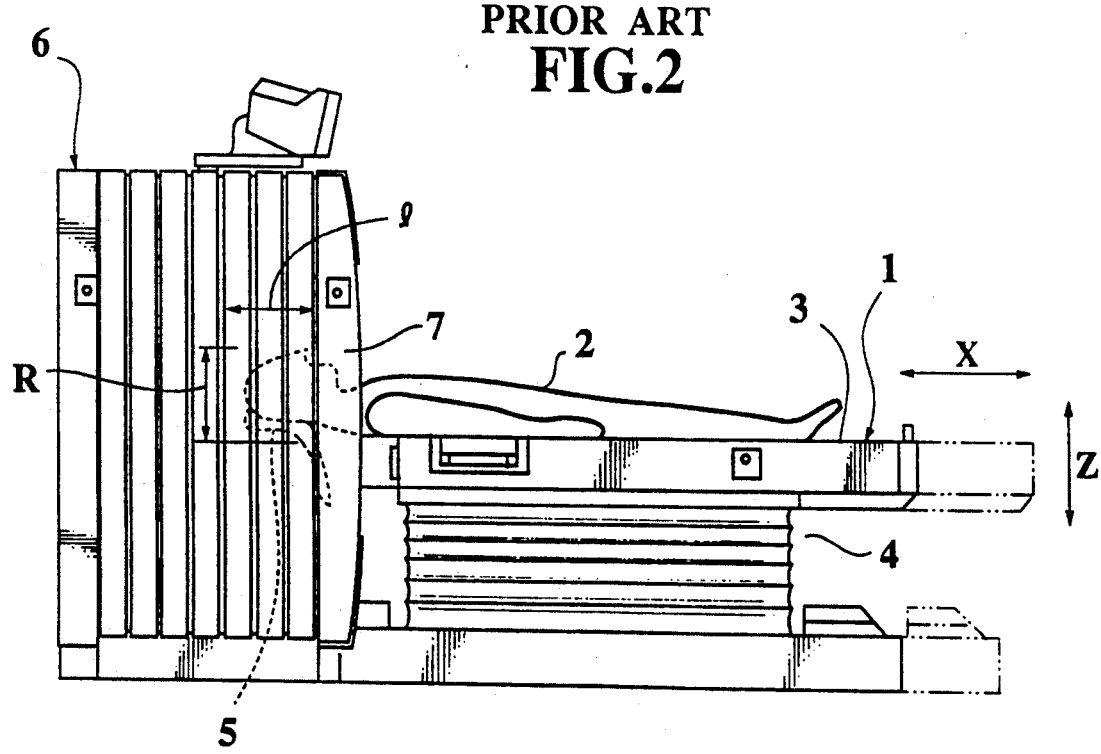
FIG. 2 is a side view of the conventional SPECT apparatus shown in FIG. 1.
Figure 3:
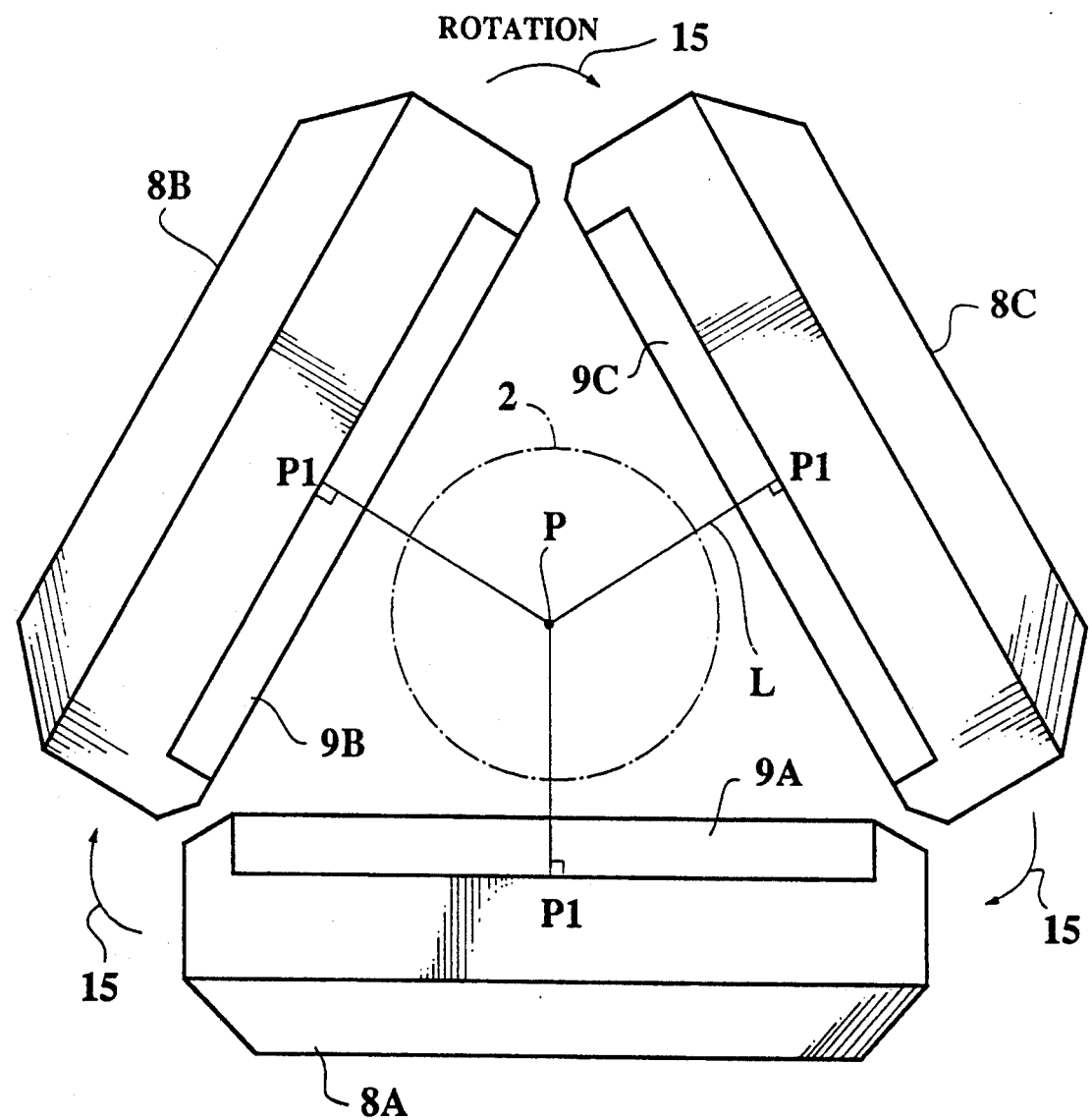
FIG. 3 is a front view of the major portion of the SPECT apparatus shown in FIG. 1.
Figure 4:
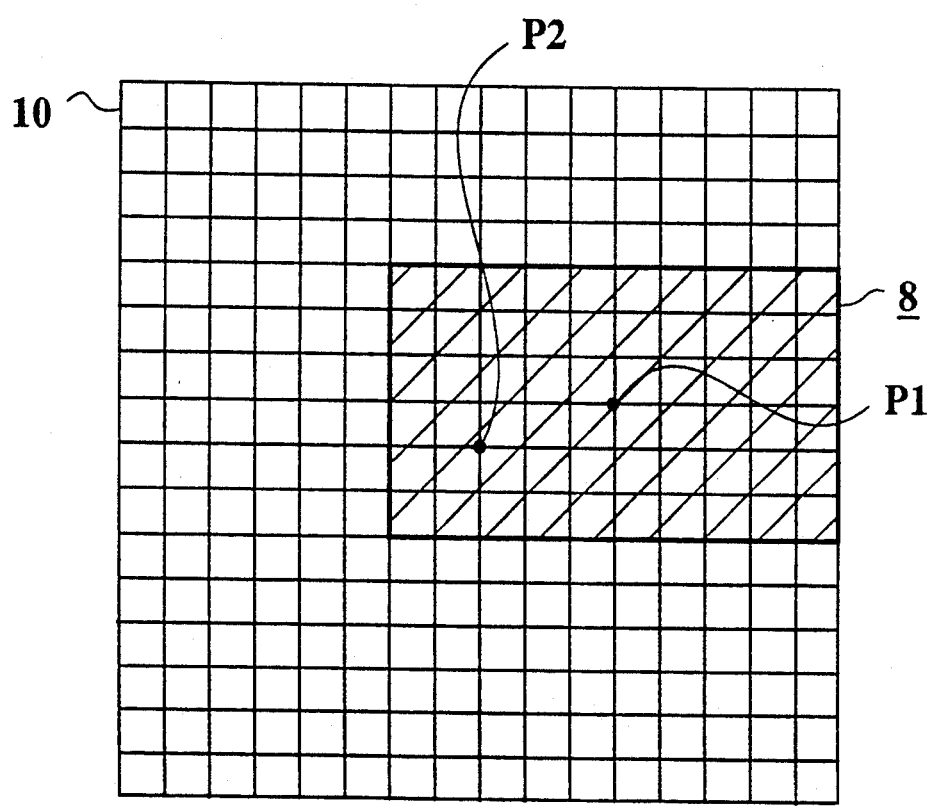
FIG. 4 is an explanatory diagram for explaining a gamma-ray detection of the SPECT apparatus.

FIG. 7A represents the major portion of a SPECT apparatus capable of performing the above-described positional-shift correction method, in which three sets of gamma-ray detectors 8A to 8C are equidistantly positioned apart from each other by 120 degrees with respect to the rotation center "P". Then, these detectors 8A to 8C are rotated by 120 degrees along an arrow 15, so that gamma rays emitted from RI contained in the biological body 2 (see FIG. 2) may be detected by three detectors 8A to 8C over a range of 360°.

FIG. 7B is a plan view of the first detector 8A, in which a point "P1" of intersection between a surface of this detector 8A and a perpendicular line "L" originated from the rotation center "P", corresponds to a geometrical center point of this detector 8A. As represented in FIG. 8, this geometrical center position "P₁" may be defined in such a manner that while measuring sizes "X" and "Y" of the detector 8A along the X and Y directions, two center lines X₀ and Y₀ of the respective edges thereof are intersected with each other at this geometrical center point "P₁".

Next, a collimated point-shaped RI source (not shown in detail) is positioned at this geometrical center point "P₁" so as to obtain first positional data $(x_a, y_a)$ on an output signal matrix (i.e., first positional-information coordinate output) of this detector 8A. It should be noted that second positional data on the output signal matrix (i.e., second positional-information coordinate output) with respect to the matrix center may be defined by $(x_0, y_0)$.

Figure 5:
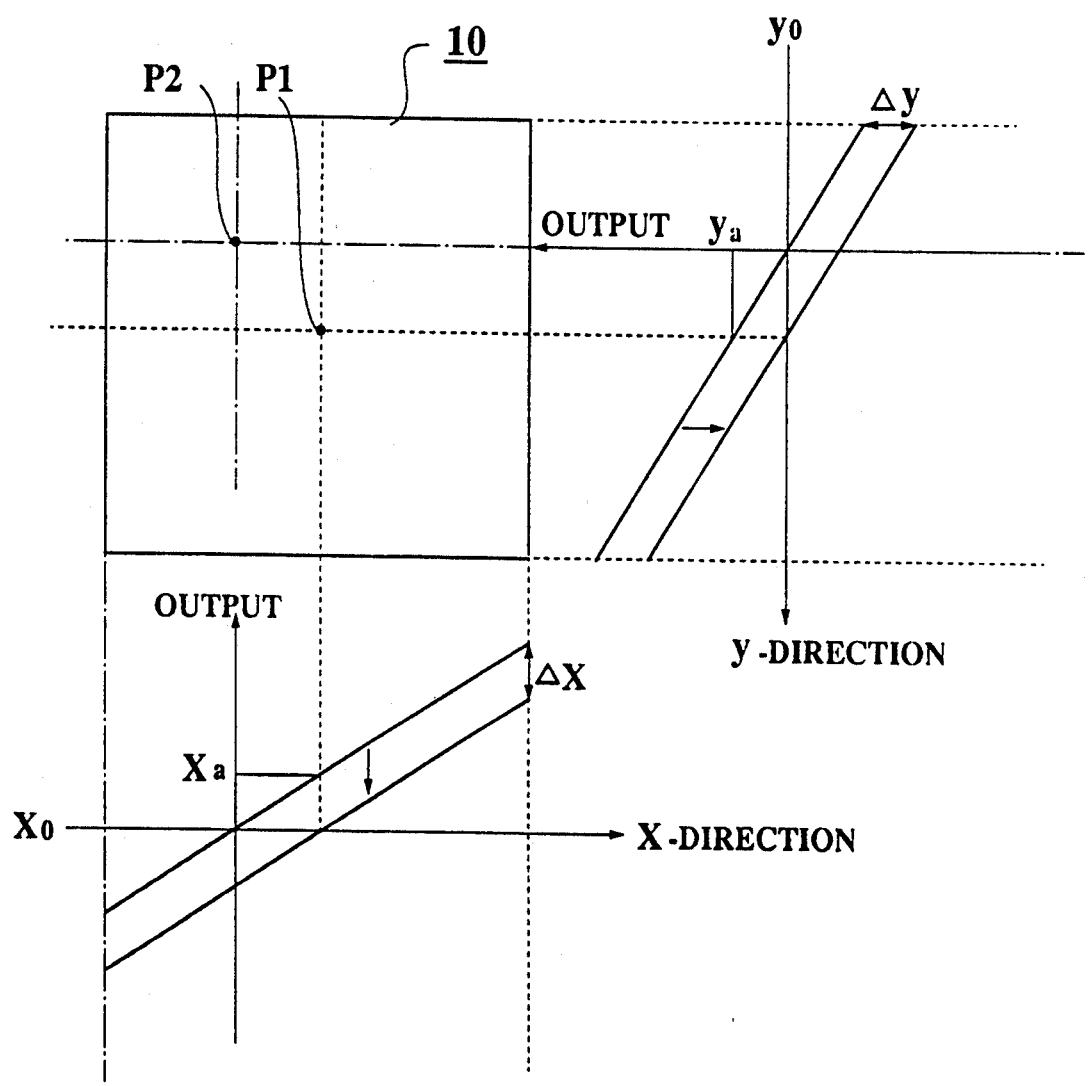
FIG. 5 is an explanatory diagram for explaining a basic idea of an offset correction method according to the present invention.

Subsequently, as represented in FIG. 5, two sets of differences "Δx" and "Δy" are calculated between the first positional data $(x_a, y_a)$ on the geometrical center position "P₁" of this detector 8A and the second positional data $(x_0, y_0)$ on the matrix's center:

$$\Delta X = x_a - x_0 \quad (1)$$

$$\Delta y = y_a - y_0 \quad (2).$$

After third positional data (X,Y) is obtained at a predetermined measuring position, this third positional data (X,Y) is subtracted by these differences ΔX and ΔY, in order that the geometrical center position "P₁" is coincident with the matrix's center position "P₂":

$$X - (x_a - x_0) \text{ and } Y - (y_a - y_0) \quad (3).$$

That is to say, as apparent from FIG. 5, correct positional data which has been offset-corrected based upon the above-described formulae may be obtained in accordance with the offset (positional-shift) correction method of the preferred embodiment.

Thus, the above-described offset correction calculation will be similarly performed with respect to the remaining gamma-ray detectors 8B and 8C.

Arrangement of SPECT Apparatus With Positional-Shift Correction

Figure 10:
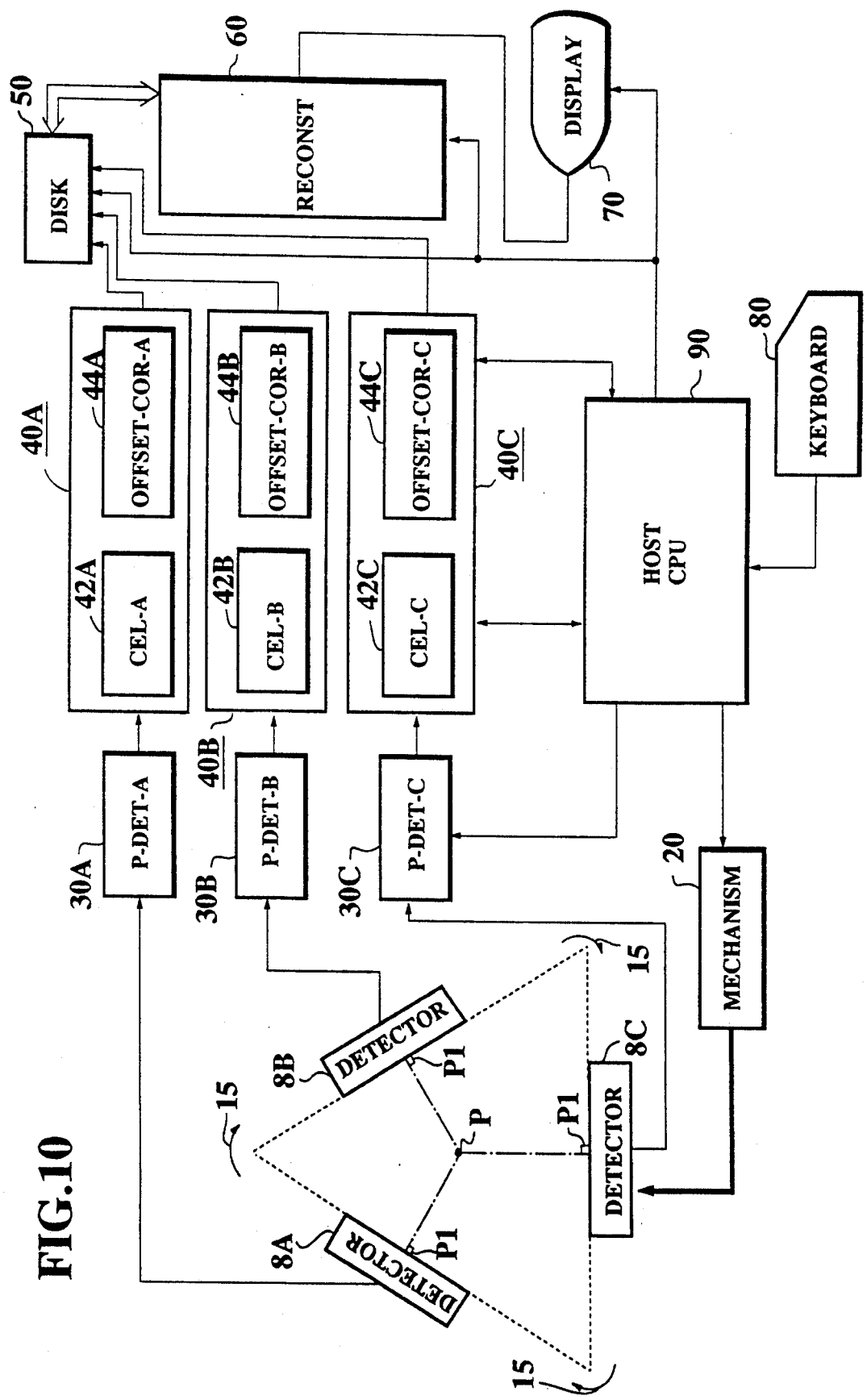
FIG. 10 is a schematic block diagram of an entire arrangement of the SPECT apparatus shown in FIG. 7.

In FIG. 10, there is shown an overall arrangement of a SPECT apparatus with an offset correction according to a preferred embodiment of the present invention.

Three sets of gamma-ray detectors 8A to 8C are equidistantly arranged in the similar way to that of FIG. 7A. These gamma-ray detectors (i.e., gamma cameras) 8A to 8C are rotatable along the rotation arrow 15 by means of a mechanism 20. An output signal of each detector 8A, 8B, 8C is processed in a series circuit of a position detector 30A, 30B, 30C, and a positional data processor 40A, 40B, 40C. Since internal arrangements of these series circuits are identical to each other, only the internal arrangement of the first series circuit will now be described more in detail.

The position detector 30A detects positional data (positional-information coordinate output) from the output signal derived from the first gamma-ray detector 8A. It should be noted that this positional data contains the above-described positional shift. To eliminate such a positional shift from the output signal of the detector 8A, namely to correct the offset positional data, the positional data processor 40A is employed. The positional data processor 40A is mainly constructed of a CEL (correction of energy and linearity) data correcting circuit 42A and an offset correcting circuit 44A (will be described in detail).

The output data of the position detector 40A is supplied to a hardware disk memory 50 such as a magnetic disk. The output data of this disk memory 50 is connected to an image reconstruction circuit 60. The reconstructed tomographic image data of the biological body 2 under medical examination is supplied to a display unit 70, whereby a tomographic image thereof is displayed on the display unit 70.

A keyboard 80 for entering various instructions is connected to a host CPU (central processing unit) 90. The host CPU 90 controls all of the above-described circuit arrangements 20, 30, 40, 50, 60, 70 and 80.

Overall Positional Correction Operation

Figure 11:
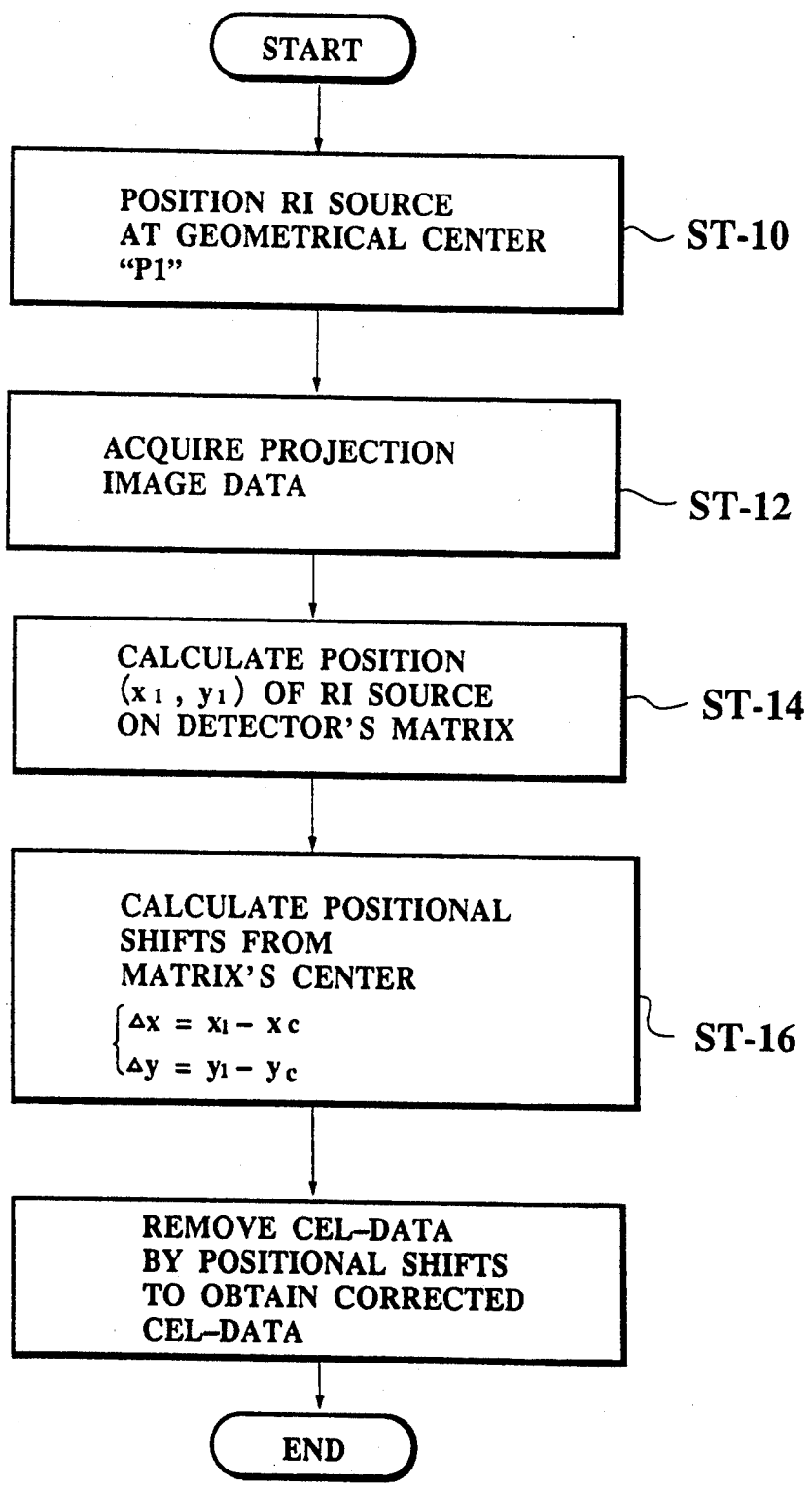
FIG. 11 is a flowchart for explaining an overall operation of the offset correction method executed in the SPECT apparatus shown in FIG. 7.

Referring now to a flowchart shown in FIG. 11, an overall positional-shift correction operation effected in the SPECT apparatus shown in FIG. 10 will be described.

At a first step ST-10, a point-shaped RI source (not shown in detail) is positioned at the geometrical center point "P₁" of each detector 8A, 8B, 8C. Then, projection image data is acquired at a step ST-12. A calculation is carried out with respect to positional data $(x_l, y_l)$ of the point-shaped RI source on the output signal matrix of the respective detectors at a step ST-14.

Furthermore, positional shifts (Δx, Δy) of the calculated positional data $(x_l, y_l)$ are calculated from the center point $(x_c, y_c)$ on the output signal matrix of the detector at a step ST-16:

$$\Delta x = x_l - x_c \quad (4)$$

$$\Delta y\ 32\ y_l - y_c \quad (5)$$

Subsequently, at a step ST-18, the previously obtained CEL data is removed by the above-described positional shift data obtained at the previous step ST-16, whereby corrected CEL data can be obtained.

Cel Data/Offset Corrections

Figure 12:
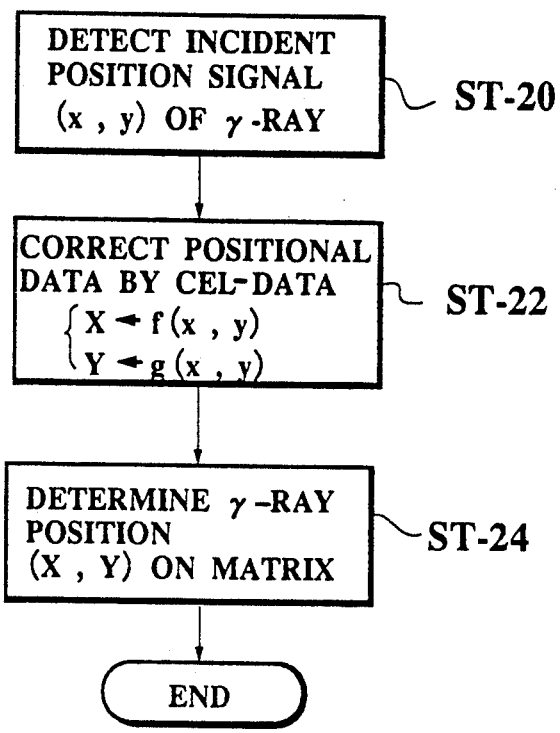
FIG. 12 is a flowchart for explaining a CEL-data correction performed in the SPECT apparatus shown in FIG. 4.

FIG. 12 is a flowchart for explaining the CEL data correction effected in the CEL data correcting circuit 42A, 42B, 42C shown in FIG. 10.

In the CEL data correction flowchart of FIG. 12, an incident position signal (x,y) of a gamma ray is detected at a step ST-20. A positional correction is carried out based upon the CEL data which corresponds to arithmetic formulae f (x,y) and g (x,y):

$$X \leftarrow f(x, y)$$

$$Y \leftarrow g(x, y).$$

Finally, a position (X,Y) of the incident gamma ray on the output signal matrix of the detector is determined.

Figure 13:
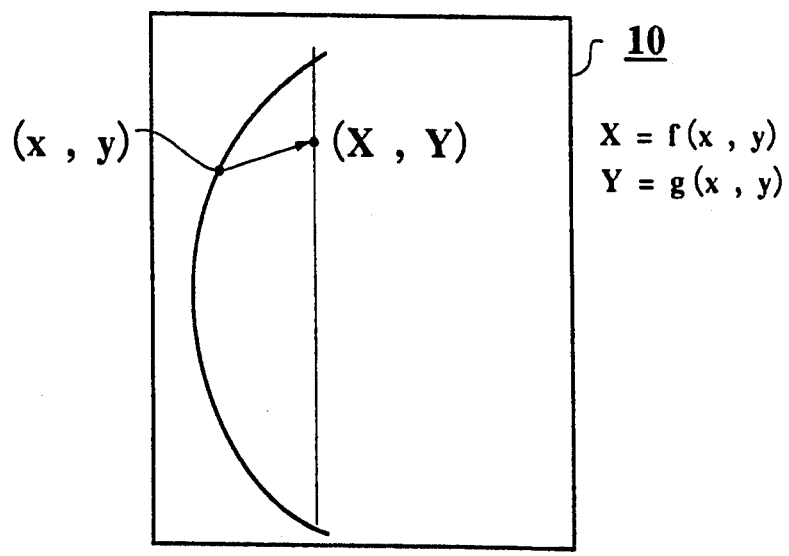
FIG. 13 pictorically represents the CEL-data correction of FIG. 12.

The above-described CEL data correction operation is pictorially represented in FIG. 13.

Internal Arrangement of Positional Data Processor

Figure 14:
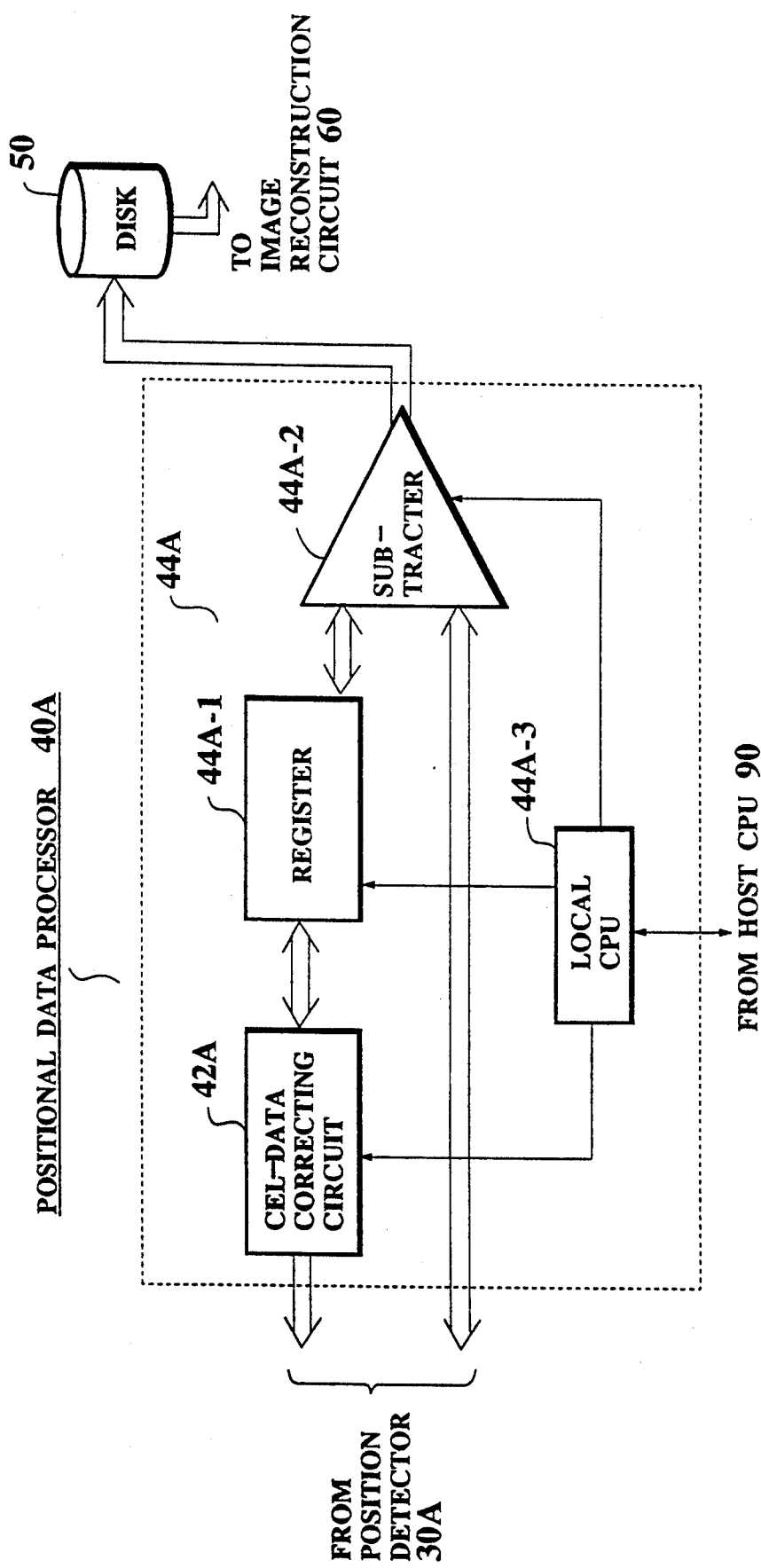
FIG. 14 is a schematic block diagram of an internal circuit arrangement of the positional data processor 40A shown in FIG. 10.

FIG. 14 is a schematic block diagram of an internal arrangement of the positional data processor 40A.

As previously described, the positional data processor 40A includes the CEL-data correction circuit 42A and the offset correction circuit 44A. This offset correction circuit 44A is constructed of a register 44A-1, a subtracter 44A-2 and a local CPU 44A-3. The input of the register 44A-1 is connected to the CEL-data correcting circuit 42A, whereas the output of the subtracter 44A-2 is connected to the disk memory 50.

Operations of this positional data processor 40A will now be described with reference to the above-described flowchart shown in FIG. 11.

Assuming now that the positional shifts Δx and Δy previously calculated and stored into a local memory (not shown in detail) employed in the CEL-data correcting circuit 42A are read out and then are temporarily stored in the register 44A-1 of the offset correction circuit 44A. Then, these positional shift data (i.e., CEL-data) are supplied to one input of the subtracter 44A-2, and also the positional data newly measured by the gamma-ray detector 8A via the position detector 30A are directly supplied to the other input of this subtracter 44A-2.

Next, the above-described calculation (3) is carried out in the subtracter 44A-2. Accordingly, the corrected positional data in which the positional-shift correction has been completed may be produced from this subtracter 44A-2 and thereafter stored in the disk memory 50.

While the present invention has been described in detail, the basic idea of the invention is not restricted to the SPECT apparatus with employment of three detectors, but may be readily applied to other types of gamma camera apparatuses.

For instance, a gamma camera apparatus with a single gamma-ray detector may be realized with employment of the aboved-explained basic idea, and also a point-shaped RI source may be positioned at a rotation center "P", instead of the geometrical center "$P_1$".

As previously described, in accordance with the present invention, after the output of the gamma-ray detector is measured under condition that the point-shaped RI source is positioned at the geometrical center position "$P_1$" of this detector, a predetermined calculation is performed on this detector's output so as to produce the correction data (namely, the corrected CEL-data, or offset correction data). Based upon this correction data, the positional shift between the geometrical center position "$P_1$" of the detector and the center position "$P_2$" of the output signal matrix there of may be readily corrected. In other words, since the geometrical center position "$P_1$" is identical to the matrix's center position "$P_2$", the ring-shaped artifact appearing in the conventional tomographic image may be prevented or considerably reduced.

What is claimed is:

1. A method for correcting a positional shift containing a positional-information coordinate output in a matrix form derived from a gamma camera apparatus having at least a first gamma-ray detector, comprising the steps of:

positioning a reference RI (radio isotope) source at a center position of the first gamma-ray detector;
    detecting a first positional-information coordinate output by said first gamma-ray detector;
    comparing said first positional-information coordinate output with a second positional-information coordinate signal corresponding to a center position of the matrix to produce positional correction data indicative of a difference between said first positional-information coordinate output and said second positional-information coordinate signal;
    acquiring by said first gamma-ray detector a third positional-information coordinate output of an RI injected into an object under medical examination; and,
    correcting the third positional-information coordinate output based upon said positional correction data.

2. A method as claimed in claim 1, wherein said center position of said gamma-ray detector is a geometrical center position on a surface of said gamma-ray detector.

3. A method as claimed in claim 1, wherein second and third gamma-ray detectors are positioned in such a manner that center positions of said first to third gamma-ray detectors are selected to be geometrical rotation centers when said first through third detectors are rotated around said object.

4. A method as claimed in claim 1, wherein said comparing step is performed by subtracting said second positional-information coordinate output from said first positional-information coordinate output, whereby said positional correction data are obtained.

5. A method as claimed in claim 1, wherein said correcting step is performed by subtracting said positional correction data from the third positional-information coordinate output.

6. A method as claimed in claim 1, further comprising: second and third gamma-ray detectors equidistantly separated from each other with reference to the first gamma-ray detector along a rotation direction.

7. A method as claimed in claim 1, wherein said reference RI source is a point-shaped RI source.

8. A gamma camera apparatus comprising:

at least a first gamma-ray detector means for obtaining a first positional-information coordinate output in a matrix form representing a first reference position by detecting gamma rays radiated from a reference RI (radio isotope) source positioned at a predetermined position with respect to said first gamma-ray detector means;
    positional-data processing means for processing the first positional-information coordinate output based upon a second positional-information coordinate signal in a matrix form indicative of a second reference position with respect to a matrix output derived from the first gamma-ray detector means to produce positional correction data;
    said first gamma-ray detector means further detecting gamma-rays emitted from a radio isotope injected into a biological body under medical examination to obtain a third positional-information coordinate output in a matrix form;
    said positional-data processing means correcting the third positional-information coordinate output based upon the positional correction data whereby positional shifts contained in the third positional-information correction output are removed.

9. A gamma camera apparatus as claimed in claim 8, wherein said positional-data processing means includes:

a CEL(correction of energy and linearity)-data correcting circuit for subtracting the second positional-information coordinate output from the first positional-information coordinate output to obtain the positional correction data; and,
    an offset correcting circuit for subtracting the positional correction data from the third positional-information coordinate data to eliminate the positional shifts from the third positional-information coordinate data.

10. A gamma camera apparatus as claimed in claim 9, wherein said offset correcting circuit is constructed of a register, a subtracter and a local CPU (central processing unit).

11. A gamma camera apparatus as claimed in claim 8, wherein said first reference position is selected to be a geometrical center position defined at a detecting surface of the first gamma-ray detector means, and the second reference position is selected to be a center position of the matrix output from the detector means.

12. A gamma camera apparatus as claimed in claim 8, wherein said first reference position is selected to be a rotation center defined while the first gamma-ray detector means is rotated, and the second reference position is selected to be a center position of the matrix output from the detector means.

13. A gamma camera apparatus as claimed in claim 8, further comprising:
    second and third gamma-ray detector means equidistantly separated from each other with reference to the first gamma-ray detector means along a rotation direction.

14. A gamma camera apparatus as claimed in claim 8, wherein said reference RI source is a point-shaped RI source.

15. A method for correcting a positional shift containing a positional-information coordinate output in a matrix form derived from a gamma camera apparatus having at least a first gamma-ray detector, comprising the steps of:
    positioning a reference RI (radioisotope) source at a predetermined position with respect to the first gamma-ray detector;
    detecting a first positional-information coordinate output by said first gamma-ray detector;
    comparing said first positional-information coordinate output with a second positional-information coordinate signal corresponding to said predetermined position on the matrix form to produce positional correction data indicative of a difference between said first positional-information coordinate output and said second positional-information coordinate signal;
    acquiring by said first detector a third positional-information coordinate output of an RI injected into an object under medical examination; and,
    correcting the third positional-information coordinate output based on said positional correction data.

16. A method as claimed in claim 15, wherein second and third gamma-ray detectors are positioned in such a manner that center positions of said first to third gamma-ray detectors are selected to be geometrical rotation centers when said first through third detectors are rotated around said object.

17. A method for correcting a positional shift containing a positional-information coordinate output in a matrix form derived from a gamma camera apparatus having at least a first gamma-ray detector, comprising the step of:
    positioning a first reference RI (radioisotope) source having a predetermined pattern on said first detector;
    detecting an output of said first reference RI source by said first detector;
    obtaining linearity-correction data to correct a non-linearity of said first detector from distortion between output of said first reference RI source and said pattern and;
    positioning a second reference RI source at a predetermined position on said first gamma-ray detector;
    detecting a positional-information coordinate output of said second reference RI source by said first detector;
    calculating an offset value between an electrical signal corresponding to said predetermined position and said positional-information coordinate output; and,
    offsetting said linearity correction data to compensate for said offset value.

18. A method as claimed in claim 17, wherein second and third gamma-ray detectors are positioned in such a manner that center positions of said first to third gamma-ray detectors are selected to be geometrical rotation centers when said first through third detectors are rotated around said object.

* * * * *